(12) United States Patent
Wieters

(10) Patent No.: US 12,207,979 B2
(45) Date of Patent: Jan. 28, 2025

(54) HOLDER FOR AN IMAGE SENSOR OF A SURGICAL INSTRUMENT

(71) Applicant: Olympus Winter & Ibe GmbH, Hamburg (DE)

(72) Inventor: Martin Wieters, Barsbuettel (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 524 days.

(21) Appl. No.: 17/563,307

(22) Filed: Dec. 28, 2021

(65) Prior Publication Data

US 2022/0202524 A1   Jun. 30, 2022

(30) Foreign Application Priority Data

Dec. 29, 2020 (DE) ............... 10 2020 135 029.5

(51) Int. Cl.
| | | |
|---|---|---|
| *A61B 1/00* | (2006.01) | |
| *A61B 1/05* | (2006.01) | |
| *A61B 90/50* | (2016.01) | |

(52) U.S. Cl.
CPC .......... *A61B 90/50* (2016.02); *A61B 1/00147* (2013.01); *A61B 1/00188* (2013.01); *A61B 1/05* (2013.01)

(58) Field of Classification Search
CPC . A61B 90/50; A61B 1/00147; A61B 1/00188; A61B 1/05; H04N 23/555; H04N 23/51; G02B 23/2484
See application file for complete search history.

(56) References Cited

U.S. PATENT DOCUMENTS

| | | | | |
|---|---|---|---|---|
| 4,745,470 A | * | 5/1988 | Yabe ............... | H04N 23/66 600/109 |
| 2009/0177038 A1 | * | 7/2009 | Yashiro ............ | H01R 13/5804 600/132 |
| 2009/0259101 A1 | * | 10/2009 | Unsai .............. | A61B 1/05 600/110 |
| 2010/0210905 A1 | * | 8/2010 | Takeuchi ......... | A61B 1/00135 600/110 |

(Continued)

FOREIGN PATENT DOCUMENTS

| | | |
|---|---|---|
| DE | 10 2015 118 199 A1 | 4/2017 |
| DE | 10 2017 105 354 A1 | 9/2018 |
| JP | 2006-061327 A | 3/2006 |

OTHER PUBLICATIONS

English abstract only of EP 3 376 273 A2.

*Primary Examiner* — Anh Tuan T Nguyen
*Assistant Examiner* — Rynae E Boler
(74) *Attorney, Agent, or Firm* — Scully, Scott, Murphy & Presser, P.C.

(57) ABSTRACT

A holder for a surgical instrument, where the holder includes: an image sensor, the image sensor having a photosensitive layer and a rear side facing away from the photosensitive layer; and a circuit board, a first side of the circuit board being connected to the rear side of the image sensor. The holder may have a cover member having a first side arranged on a second side of the circuit board, the second side of the circuit board facing away from the image sensor. The cover member may be configured to form an interspace between the first side of the cover member and the second side of the circuit board, and the interspace may be filled with an adhesive.

19 Claims, 3 Drawing Sheets

(56) References Cited

U.S. PATENT DOCUMENTS

| | | | | |
|---|---|---|---|---|
| 2011/0092769 | A1* | 4/2011 | Kokubo | A61B 1/128 |
| | | | | 600/109 |
| 2012/0220825 | A1* | 8/2012 | Kimura | A61B 1/00124 |
| | | | | 600/109 |
| 2015/0305601 | A1* | 10/2015 | Levi | A61B 1/00181 |
| | | | | 600/109 |
| 2015/0340133 | A1* | 11/2015 | Jungbauer | H05K 1/0298 |
| | | | | 600/109 |
| 2017/0071462 | A1* | 3/2017 | Wieters | A61B 1/043 |
| 2017/0112369 | A1 | 4/2017 | Czupalla | |
| 2018/0020904 | A1* | 1/2018 | Wieters | G02B 23/243 |
| | | | | 600/109 |

\* cited by examiner

HOLDER FOR AN IMAGE SENSOR OF A SURGICAL INSTRUMENT

CROSS-REFERENCE TO RELATED APPLICATION

The present application is based upon and claims the benefit of priority from DE 10 2020 135 029.5 filed on Dec. 29, 2020, the entire contents of which is incorporated herein by reference.

BACKGROUND

Field

The present disclosure relates generally to a holder for a surgical instrument, such as for an endoscope or video endoscope, having an image sensor. Moreover, the present disclosure relates to a surgical instrument, such as an endoscope or video endoscope.

Prior Art

Endoscopes, such as, video endoscopes, in which the light of a surgical field entering at a distal tip of an endoscope shaft of the endoscope is directed through an optical system onto a proximal ocular or one or more image sensors, are known in different designs. Thus, there are endoscopes with a direct view, known as a 0° viewing direction, or endoscopes with a lateral viewing direction, which have, for example, a lateral viewing direction of 30°, 45°, 70° or similar deviating from the 0° viewing direction. The named degree numbers hereby mean the polar angle between the central viewing axis and the longitudinal axis of the endoscope shaft. There are also endoscopes or respectively video endoscopes with an adjustable lateral viewing direction, in which the viewing angle, i.e., the deviation from the direct view, is adjustable. Besides an adjustment of the viewing angle, i.e., of the deviation from the direct view, the viewing direction, i.e., the azimuth angle, can also be adjusted around the longitudinal axis of the endoscope shaft, in that the endoscope is rotated in its entirety around the longitudinal axis of the endoscope shaft.

It is also known to arrange the image sensor in video endoscopes not vertically but horizontally to the endoscope shaft axis. For this purpose, the image sensor is glued to a deflecting prism, wherein the light entry face of the prism is arranged perpendicular and the light exit face of the prism parallel to the endoscope axis.

SUMMARY

Proceeding from this prior art, an object is to improve the stable positioning and secure alignment of an image sensor of an endoscope in a simple manner.

Such object can be solved by a holder for a surgical instrument, such as endoscope or video endoscope, having an image sensor, with an image sensor, such as a CCD sensor or CMOS sensor, wherein the image sensor has a photo-sensitive layer and a rear side facing away from the photo-sensitive layer, wherein the image sensor is connected, such as being soldered, on its rear side to a circuit board for the image sensor.

By attaching the image sensor to the circuit board, such as by soldering the circuit board to the image sensor, the image sensor can be permanently positioned, as a result of which the fixed image sensor does not move in relation to the rest of the optical system of the surgical instrument, for example, for the service life of an endoscope, so that the imaging quality of the captured images is improved.

By way of the circuit board, the individual units of the photo-sensitive layer can be contacted to supply them with power and transmit the received information. The image sensor can be soldered to the circuit board, for example using flip-chip technology. The circuit board can be produced, for example, from composite materials, consisting, for example, of epoxy resin and glass fiber fabric or of polyimide. The circuit board can have a high inherent rigidity and dimensional stability. The circuit board can be produced, for example, from a composite material of the class FR4.

In one embodiment of the holder, the circuit board can be configured as a ceramic circuit board or the circuit board can be produced from polyimide or from a composite material.

The image sensor and the circuit board can be connected to each other by means of a flip-chip assembly method. For example, the circuit board and the image sensor can be soldered to each other.

For secure positioning, for example within a sleeve, a cover member can be arranged on the side of the circuit board facing away from the image sensor.

In addition, an interspace, such as being formed along the longitudinal extension of the circuit board, can be formed between the cover member and the rear side of the circuit board, wherein the interspace between the cover member and the rear side of the circuit board can be filled with an adhesive. By filling the interspace between the cover member and the rear side of the circuit board with an adhesive, a fixed connection between the cover member and the circuit board is formed, as a result of which the handling of the holder overall can be improved.

To form the interspace between the cover member and the rear of the circuit board, the cover member can have at least one or more distancing members on the side facing the circuit board, wherein the distancing member or the distancing members can be brought into contact with the circuit board. For example, multiple distancing members can be arranged on the side of the cover member facing the circuit board, wherein the distancing members can be formed, for example, as feet or the like. In this case, the distancing members can be the same height from the base area of the cover member. In one embodiment, three or more distancing members can be arranged on the side of the cover member facing the circuit board to form an interspace between the cover member and the circuit board.

The holder can have a sleeve for accommodating the image sensor and the circuit board, wherein the image sensor and the circuit board can be accommodated or arranged in the sleeve. In addition, additional devices, such as optical assemblies or the like can be accommodated in the sleeve.

The sleeve can have an accommodation opening for accommodating the cover member, wherein the cover member can be arranged in the accommodation opening of the sleeve. By accommodating the cover member in the accommodation opening of the sleeve, an exact alignment and positioning of the image sensor can be enabled, wherein the accommodation opening can be formed as a fit for the cover member.

Furthermore, at least one gap and/or at least one pocket can be formed between the cover member and the accommodation opening, wherein the at least one gap and/or the at least one pocket can be filled with an adhesive. As a result, the cover member can be glued in the accommodation opening to the sleeve, as a result of which an exact alignment of the image sensor connected thereto in the sleeve can be achieved in relation to an optical assembly, for example with a prism. The cover member can be formed as an elongated member, wherein the longitudinal extension of the cover member can be aligned parallel to the longitudinal extension of the sleeve and/or of the endoscope shaft of the surgical instrument.

The cover member can have one or more, such as two, recesses on one head end or on each of the two head ends, as a result of which, for example, pockets can be formed between the cover member and the accommodation opening, which surrounds the cover member, of the sleeve, into which pockets an adhesive can be introduced or applied to glue the cover member in the accommodation opening.

In addition, the interspace between the circuit board and the cover member and the at least one gap and/or the at least one pocket between the cover member and the accommodation opening of the sleeve can be connected to each other, so that, when applying an adhesive in the gap and/or the at least one pocket, the adhesive can also be introduced into the interspace between the circuit board and the cover member. As a result, the hollow spaces between the circuit board and the cover member and between the cover member and the accommodation opening of the sleeve can be provided with adhesive during assembly.

In order to form a secure alignment of the cover member within the accommodation opening of the sleeve, the cover member can have at least one, such as lateral, position marking, such as at least one protrusion and/or at least one notch, wherein the at least one position marking of the cover member can each interact with a contour, which can be complementary in shape and/or function, of the accommodation opening of the sleeve, such as notch and/or protrusion. For example, the cover member can have, as a position marking on one or on both longitudinal sides of the cover member, lateral protrusions and wings, which interact with corresponding notches in the contour of the accommodation opening, as a result of which an exact positioning of the cover member within the accommodation opening can be achieved.

An optical assembly can be arranged in the sleeve, wherein the optical assembly can be connected, such as by being glued, to the image sensor. Here, the image sensor can have a cover pane that can be connected to the photosensitive layer of the image sensor and to the optical assembly on the other side, such as by an optical adhesive.

The optical assembly can have at least one prism, such as a deflecting prism or 90° prism, wherein one or the prism of the optical assembly can be connected, such as by being glued, to the image sensor.

Furthermore, the or one prism of the optical assembly arranged in the sleeve can have a light entry face and a light exit face, wherein the light entry face of the prism can be aligned perpendicular to the longitudinal axis of the sleeve and the light exit face of the prism can be aligned parallel to the longitudinal axis of the sleeve and wherein the image sensor can be arranged parallel to the light exit face of the prism. As a result, a compact configuration and arrangement of the optical assembly together with the image sensor arranged and aligned in the sleeve can be achieved.

Furthermore, such object can be solved by a surgical instrument, such as endoscope or video endoscope, with a holder for an image sensor, such as a CCD sensor or CMOS sensor, as described above. We expressly refer to the above explanations in order to avoid repetitions.

In an embodiment of the surgical instrument, the surgical instrument has a shaft, such as an endoscope shaft, that can be introduced into a member cavity of a living being, wherein the holder is arranged in the shaft, such as on the distal end of the shaft.

BRIEF DESCRIPTION OF THE DRAWINGS

Further features will become evident from the description of embodiments, together with the claims and the appended drawings. Embodiments can fulfill individual features or a combination of several features.

The embodiments are described below, without restricting the general idea of the invention, based on exemplary embodiments in reference to the drawings, whereby we expressly refer to the drawings with regard to the disclosure of all details that are not explained in greater detail in the text. In the drawings.

In the drawings, the same or similar elements and/or parts are, in each case, provided with the same reference numerals such that they are not introduced again in each case.

DETAILED DESCRIPTION

Figure 1:
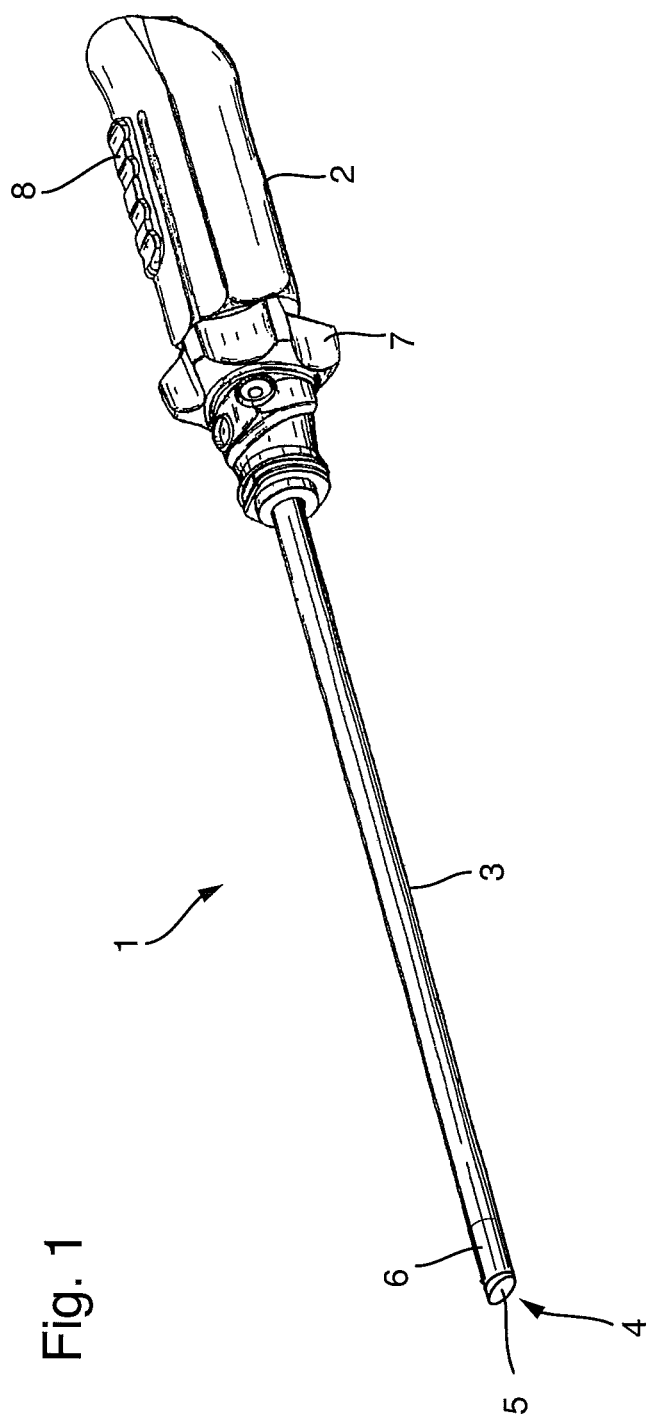
FIG. 1 illustrates a schematic, perspective representation of an endoscope.

FIG. 1 shows a schematic perspective representation of an endoscope 1 with a proximal handle 2 and a rigid endoscope shaft 3. A viewing window 5 is arranged at the distal tip 4 of the endoscope shaft 3, behind which viewing window a distal portion 6 of the endoscope shaft 3 is arranged, which distal portion has a prism unit (not shown) and an image sensor (not shown). The endoscope 1 can be configured as a video endoscope.

The viewing window 5 at the distal tip 4 is configured to be curved and asymmetrical. The viewing window 5 is thereby configured to support a variable lateral viewing angle. A change in the viewing direction, i.e., a change in the azimuthal angle about the longitudinal axis of the endoscope shaft 3 is effectuated by a rotation of the handle 2 about the central rotational axis, or longitudinal axis, of the endoscope shaft 3. The cladding tube of the endoscope shaft 3 is connected to the handle 2. The prism unit (not shown) on the distal tip 4 also rotates with the rotation of the handle 2.

The handle 2 has a first operating element configured as a rotary wheel 7 and a second operating element configured as a slide 8.

To retain the horizontal position of the displayed image, the rotary wheel 7 is held while rotating the handle 2. This causes the image sensor 24 within the interior of the endoscope shaft 3 to not follow the movement.

In order to change the viewing angle, i.e., the deviation of the viewing direction from the direct view, the slide 8 is moved. Sliding the slide 8 in the distal direction causes, for example, an enlargement of the viewing angle, moving the slide 8 back in the proximal direction causes in this case a reduction of the viewing angle to a direct view. The actuation of the slide 8 is associated with a rotation of the image sensor 24 in order to retain the horizontal position of the displayed image even when the prism unit is rotated.

Figure 2A:
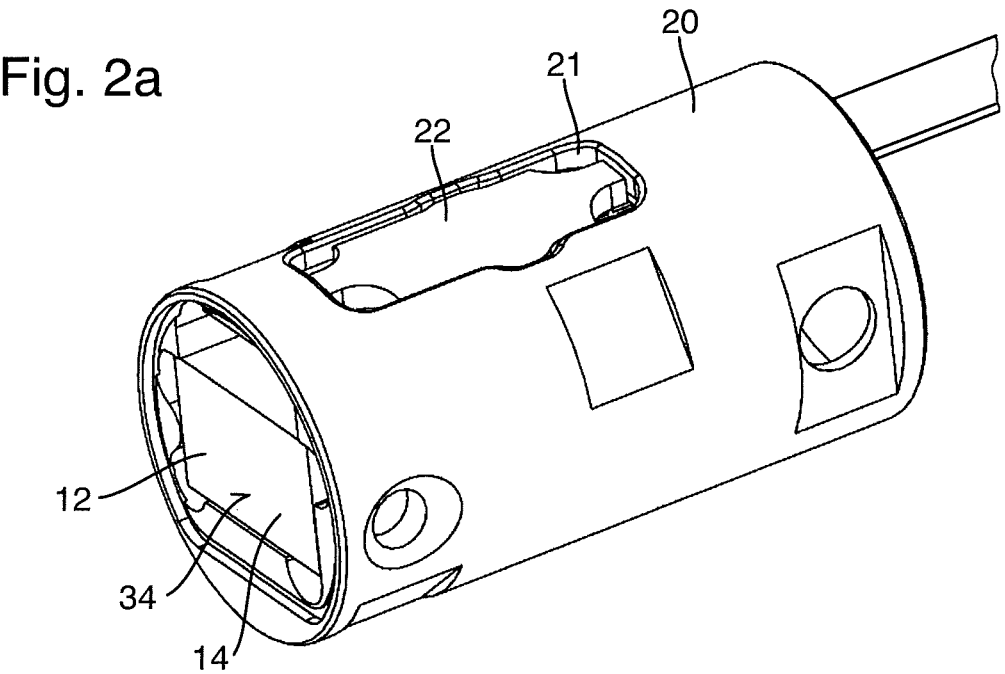
FIG. 2a schematically illustrates a view of a holder for an image sensor in a perspective view.
Figure 2B:
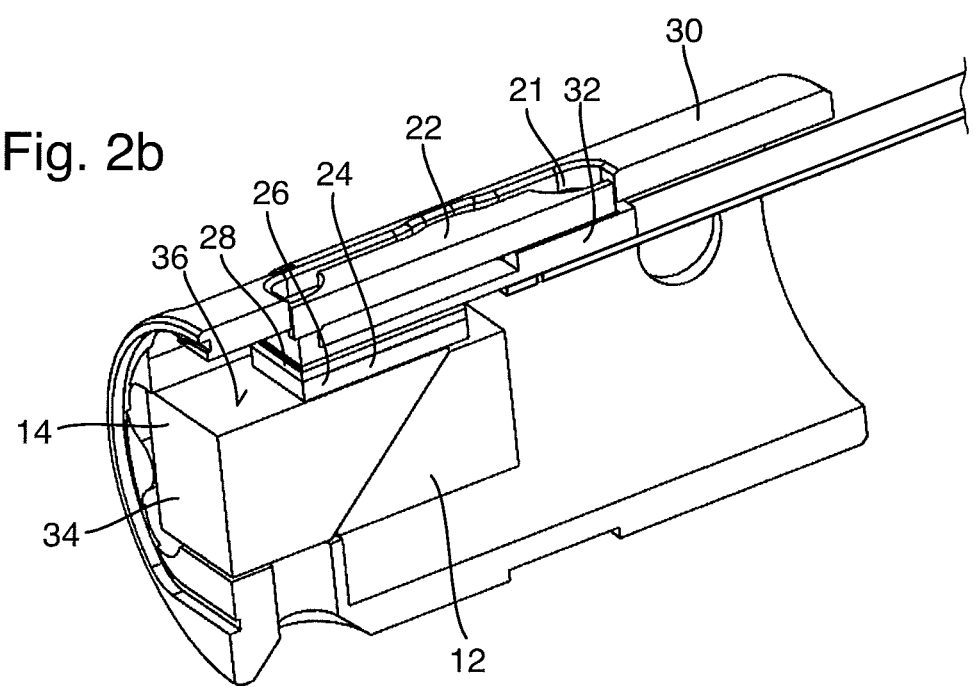
FIG. 2b schematically illustrates a cross-section through the holder for the image sensor in a longitudinal section.
Figure 2C:
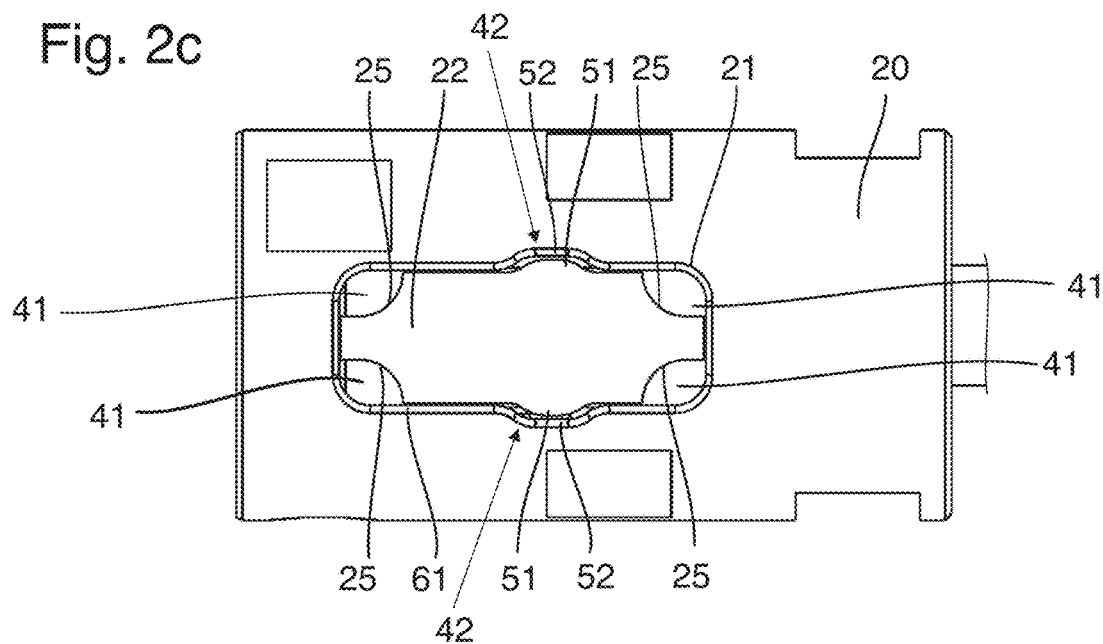
FIG. 2c illustrates a top view of the holder for the image sensor.

FIG. 2a shows a perspective view of a holder for an image sensor. FIG. 2b shows a longitudinal section through the holder. FIG. 2c shows a top view of the holder.

The holder for the image sensor 24 can be formed or arranged on the distal end of the endoscope shaft 3. In this case, the holder has a sleeve 20, wherein an optical assembly 12 with a prism 14 arranged on the distal side is arranged in the interior of the sleeve 20. The prism 14 is configured as a deflecting prism with a cuboid portion, wherein the light entry face 34 is arranged in a plane perpendicular to the longitudinal axis of the endoscope shaft 3. Furthermore, the prism 14 has a light exit face 36 (cf. FIG. 2b), wherein the light exit face 36 is aligned in a plane parallel to the longitudinal axis of the endoscope 1. An image sensor 24 is arranged on the light exit face 36 of the prism 14 so that the light beams deflected by the prism 14 are captured by the image sensor 24. The image sensor 24 can be connected on the light exit face 36 of the deflecting prism 14 by an adhesive.

Figure 4:
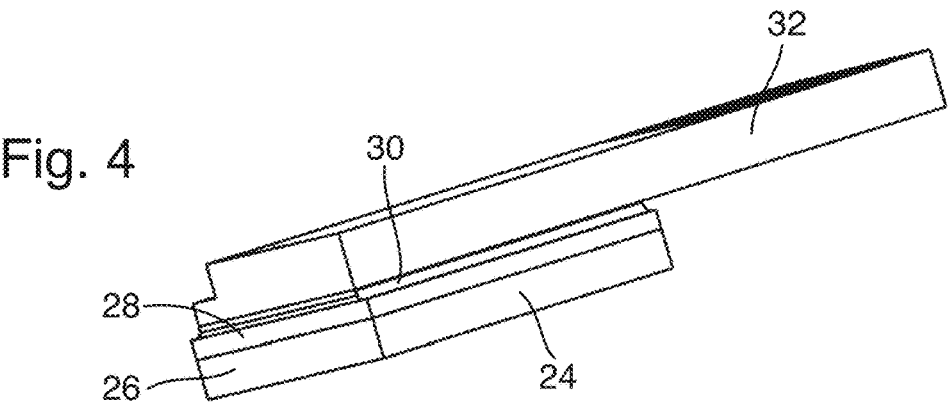
FIG. 4 schematically illustrates a perspective view of a held image sensor.

A detailed view of the image sensor 24 is shown in FIG. 4. Here, the image sensor 24 has a cover pane 26 that faces the deflecting prism 14 and is connected to a photo-sensitive layer 28 of the image sensor 24. The photo-sensitive layer 28 is provided here to convert the received light beams into corresponding electrical signals. The image sensor 24 is firmly connected on its rear side to the circuit board 32 via soldering 30. The circuit board 32 has corresponding lines which are electrically connected, for example, to the corresponding photocells of the photo-sensitive layer 28.

The dimensionally stable circuit board 32 can also be connected to the rear side of the photo sensor 24 by means of an adhesive mass.

A cover member 22 is arranged on the side of the circuit board 32 facing away from the image sensor 24 (cf. FIG. 2b), wherein an interspace is formed between the circuit board 32 and the cover member 22, which interspace can be filled with an adhesive.

In order to exactly position the cover member 22 together with the circuit board 32 and the image sensor 24 connected thereto, an accommodating opening 21 is provided in the sleeve 20, in which recess accommodating opening, the cover member 22 is accommodated (cf. FIG. 2b, 2c).

Figure 3:
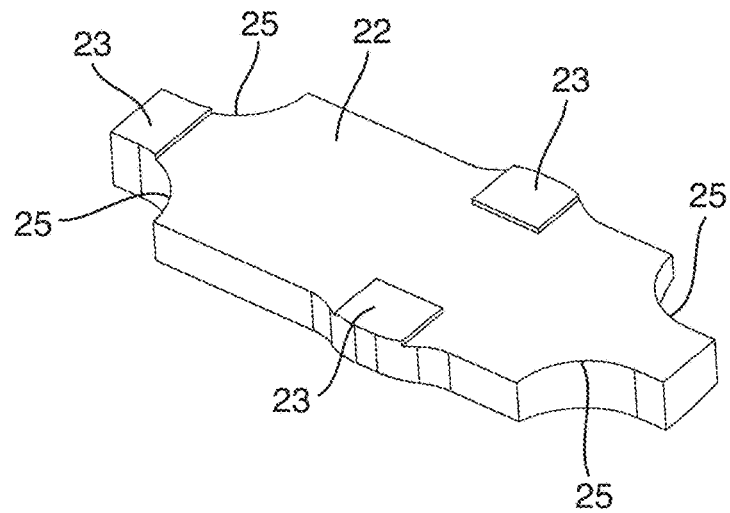
FIG. 3 schematically illustrates a perspective view of a cover member.

FIG. 3 shows a perspective view of the cover member 22, wherein here the side facing the circuit board 32 can be seen. The cover member 22 has distancing members 23 at multiple points in order to form an interspace between the cover member 22 and the circuit board 32. In addition, the cover member 22 has recesses 25 on the end faces so that, between the recesses 25 and an accommodation opening 21 of the sleeve 20, a gap (pocket) 41 is formed, and adhesive is introduced into the gaps (pockets) 41 formed as a result between the cover member 22 and the accommodation opening 21, wherein the adhesive is introduced or respectively flows from the gaps (pockets) 41 and into the interspace between the underside of the cover member 22 and the circuit board 32 through the filling of the gaps 41 (pockets). After the adhesive has cured, the circuit board 32 together with the image sensor 24 attached therein and together with the cover member 22 is aligned and fixed within the sleeve 20.

In order to form a secure alignment of the cover member 22 within the accommodation opening of the sleeve 20, the cover member 22 can have at least one, such as lateral, position marking 42, such as having at least one protrusion 51 and/or at least one notch 52 in a contour 61 of the accommodation opening 21, wherein the at least one protrusion 51 of the cover member 22 can each interact with the a corresponding notch 52, which can be complementary in shape and/or function, of the accommodation opening 21 of the sleeve 20, such as a notch and/or protrusion. For example, the cover member 22 can have, as a position marking on one or on both lateral longitudinal sides of the cover member 22, protrusions 51, which interact with corresponding notches 52 in the contour 61 of the accommodation opening 21, as a result of which an exact positioning of the cover member 22 within the accommodation opening 21 can be achieved.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMBERS

1 Endoscope
2 Handle
3 Endoscope shaft
4 Distal tip
5 Viewing window
6 Distal portion
7 Rotary wheel
8 Sliding switch
12 Optical assembly
14 Deflecting prism
20 Sleeve
21 Opening
22 Cover member
23 Distancing member
24 Image sensor
25 Recess
26 Cover pane
28 Photo-sensitive layer
30 Soldering
32 Circuit board
34 Light entry face
36 Light exit face
41 Gap (Pocket)
42 Position marking/Lateral position marking
51 Protrusion
52 Notch
61 Contour

What is claimed is:

1. A holder for a surgical instrument, the holder comprising:
an image sensor, the image sensor having a photo-sensitive layer and a rear side facing away from the photo-sensitive layer;
a circuit board having a first side and a second side, the first side of the circuit board being connected to the rear side of the image sensor;
a cover member having a first side arranged on the second side of the circuit board, the second side of the circuit board facing away from the image sensor; and
a sleeve for accommodating the image sensor and the circuit board, wherein the image sensor and the circuit board are accommodated or arranged in an interior of the sleeve;

wherein the sleeve has an accommodation opening for accommodating the cover member in the accommodation opening;

at least one gap is formed between the cover member and the accommodation opening; and the at least one gap is filled with an adhesive.

2. The holder according to claim 1, wherein the rear side of the image sensor is connected to the first side of the circuit board by soldering.

3. The holder according to claim 1, wherein the circuit board is formed from one of ceramic, polyimide or a composite material.

4. The holder according to claim 1, wherein the cover member is configured to form an interspace between the first side of the cover member and the second side of the circuit board.

5. The holder according to claim 4, wherein the interspace is filled with the adhesive.

6. The holder according to claim 4, wherein the cover member has one or more distancing members on the first side facing the second side of the circuit board to form the interspace.

7. The holder according to claim 6, wherein the one or more distancing members contact the second side of the circuit board.

8. The holder according to claim 4, wherein the interspace between the second side of the circuit board and the first side of the cover member is in communication with the at least one gap between the cover member and the accommodation opening of the sleeve.

9. The holder according to claim 1, wherein the cover member and the accommodation opening of the sleeve have at least one position marking, wherein the at least one position marking comprises the cover member having a protrusion interacting with a complementary notch in a contour of the accommodation opening of the sleeve.

10. The holder according to claim 9, wherein the at least one position marking is provided on a lateral side of each of the cover member and the accommodation opening.

11. The holder according to claim 1, further comprising an optical assembly arranged in the sleeve.

12. The holder according to claim 11, wherein the optical assembly is glued to the image sensor.

13. The holder according to claim 11, wherein the optical assembly further comprises at least one prism connected to the image sensor.

14. The holder according to claim 13, wherein the at least one prism is glued to the image sensor.

15. The holder according to claim 13, wherein the at least one prism has a light entry face and a light exit face, wherein the light entry face is aligned perpendicular to a longitudinal axis of the sleeve and the light exit face is aligned parallel to the longitudinal axis of the sleeve and wherein the image sensor is arranged parallel to the light exit face.

16. A surgical instrument comprising:

the holder according to one of claim 1.

17. The surgical instrument according to claim 16, wherein the surgical instrument comprising a shaft, the holder being arranged in the shaft.

18. The surgical instrument according to claim 17, wherein the holder being arranged at a distal end of the shaft.

19. A holder for a surgical instrument, the holder comprising:

an image sensor, the image sensor having a photo-sensitive layer and a rear side facing away from the photo-sensitive layer;

a circuit board having a first side and a second side, the first side of the circuit board being connected to the rear side of the image sensor;

a cover member having a first side arranged on the second side of the circuit board, the second side of the circuit board facing away from the image sensor; and a sleeve for accommodating the image sensor and the circuit board, wherein the image sensor and the circuit board are accommodated or arranged in an interior of the sleeve;

wherein the sleeve has an accommodation opening for accommodating the cover member in the accommodation opening;

wherein the cover member is configured to form an interspace between the first side of the cover member and the second side of the circuit board;

at least one gap is formed between the cover member and the accommodation opening and the interspace between the second side of the circuit board and the first side of the cover member is in communication with the at least one gap between the cover member and the accommodation opening of the sleeve.

* * * * *